United States Patent
Koven et al.

[11] Patent Number: 5,172,697
[45] Date of Patent: Dec. 22, 1992

[54] CUFF INFLATION SYSTEM

[75] Inventors: Paul G. Koven, St. Louis, Mo.; Yasushi Hayashi, Miyazaki, Japan

[73] Assignee: Hayashi Denki Co. Ltd., Kawasaki, Japan

[21] Appl. No.: 527,931

[22] Filed: May 24, 1990

[51] Int. Cl.$^5$ ................................................ A61B 5/02
[52] U.S. Cl. .................... 128/679; 128/677; 128/684; 128/670
[58] Field of Search ............... 128/677, 679, 684, 686, 128/672, 670, 674, 682, 687, 681, 900

[56] References Cited
U.S. PATENT DOCUMENTS

| | | | |
|---|---|---|---|
| 2,437,861 | 6/1944 | Rohr | 128/684 |
| 3,542,011 | 11/1970 | Langenbeck | 128/677 |
| 3,543,745 | 12/1970 | Rosenstein | 128/684 |
| 3,906,939 | 9/1975 | Aronson | 128/680 |
| 3,911,903 | 10/1975 | Gee et al. | 128/688 |
| 4,033,336 | 7/1977 | Murawski et al. | 128/682 |
| 4,141,346 | 2/1979 | Dean, Jr. et al. | 128/676 |
| 4,252,127 | 2/1981 | Gemelke | 128/680 |
| 4,328,810 | 5/1982 | Hill et al. | 128/680 |
| 4,356,827 | 11/1982 | Uemura et al. | 128/680 |
| 4,572,199 | 2/1986 | LaCourse | 128/657 |
| 4,649,928 | 3/1987 | Samaras et al. | 128/670 |
| 4,669,485 | 6/1987 | Russell | 128/679 |
| 4,969,466 | 11/1990 | Brooks | 128/677 |

FOREIGN PATENT DOCUMENTS 2821037 6/1979 Fed. Rep. of Germany .
1379014 10/1963 France .

Primary Examiner—Max Hindenburg
Assistant Examiner—Guy V. Tucker
Attorney, Agent, or Firm—Kalish & Gilster

[57] ABSTRACT

A cuff-inflation system for inflating a blood pressure cuff is provided with an activating and control assembly. The activating and control assembly includes a first connector port with an attached internal tube and a second connector port with an attached internal tube that is adapted to intersect and join the first internal tube. A miniature electric pump is connected to the first internal tube and there is further provided an activating switch for activating the system. A first external tubular connector connects the activating and control assembly to a blood pressure cuff and a second external tubular connector connects the activating and control assembly to a pressure regulating device.

11 Claims, 5 Drawing Sheets

CUFF INFLATION SYSTEM

BACKGROUND OF THE INVENTION

The present invention generally relates to blood pressure cuff inflators and, more particularly is concerned with a miniaturized electronic cuff inflator interfaced with a pressure adjusting device such as a sphygmomanometer or a mercury manometer.

DESCRIPTION OF THE PRIOR ART

In general, electronic cuff inflators are being used in the field of medical vascular testing. These devices are characterized by the following features: (a) a cuff having a single connector; (b) a built in pressure level monitor of the aneroid or digital read-out type; (c) a bleed rate control located on the face of the unit; (d) typically large in size, that is, not miniaturized; (e) a very fast inflation cycle that is typically incompatible with small cuffs; and (f) a pressure level monitor requiring calibration. Thus, prior art cuff inflators present certain problems and shortcomings as a result of the aforementioned characteristics.

A single connector cuff inflator has an inherently rigid inflate cycle, wherein the single connector dedicates the inflator to a cuff only. There is no provision contained in an inflator of this construction for manual sphygmomanometer assisted incremental inflation or deflation. This shortcoming is especially acute when using small cuff inflators for digit and penile applications. Small cuffs inflate too quickly for useful measurements and cuff damage frequently occurs due to over-inflation.

It is of diagnostic importance in vascular blood pressure and pulse-volume testing to be certain the blood pressure level is accurate. Calibration requires the use of a mercury manometer in line with the inflator connector and the cuff. Comparisons are then taken of the pressure levels from the manometer and the pressure gauge on the cuff inflator. This is an off line procedure resulting in calibration of prior art cuffs before they can be thus used.

Prior art cuff inflators commonly employ a variable bleed control. It opens the closed loop between the cuff and inflator to the atmosphere. This control is used for setting cuff deflation rate and must be closed off prior to cuff inflation. This causes the bleed rate control to remain in the "open" position after deflation. A difficulty arises due to operator forgetfulness frequently causing the cuff to be re-inflated. In addition, multiple controls on a cuff inflator are disadvantageous to operators and handicapped health care personnel. Operators frequently work with a Doppler probe in one hand while adjusting an instrument such as a sensing recorder in the other. There is, therefore, no provision for manual incremental inflation or deflation by the operator.

Another prior art problem occurs when multiple cuffs on the same limb site are used. Inflators are known to have an effect on blood pressure results. The operator typically must reach over to the inflators to make adjustments in the deflation rate. This is an inconvenient extra step. It often causes rapid deflation that may exceed the recommended bleed rate frequently necessitating the repetition of a test. Conversely, small cuff inflation adjustment is very difficult to achieve because of the fast inflate characteristics of the inflator. This fast inflation rate often causes ruptured cuff bladders.

A further problem associated with cuff inflators of the prior art is their bulky nature resulting in cumbersome instruments. This inhibits mobility in certain mobile emergency situations.

Thus, the problems of the prior art have demonstrated the need for a cuff inflation system that provides simultaneous inflation and monitoring of the cuff pressure.

SUMMARY OF THE INVENTION

The present invention is a miniaturized cuff inflator interfaced with a pressure adjusting device such as a sphygmomanometer or mercury manometer. The cuff inflator of this invention is provided with two tubular connectors, one fastened to a blood pressure cuff and the second tube connected to a pressure adjusting device so that pressure control and monitoring of the blood pressure cuff can be readily facilitated.

The cuff inflation system of the present invention contains an activating and power control assembly having two ports, and fastened to each port are internal tubular connectors. It is further provided for one tube to intersect with the second tube so that a single tubular connector is fastened to a pump motor that serves to inflate the blood pressure cuff and the pressure adjusting device. The pump motor may be further provided with a one shot multi-vibrator circuit for deactivating the pump motor after a predetermined time interval. An electric circuit having a switch is connected to the pump motor drive circuit for activating the cuff inflator and deactivating the power supply when a predetermined inflation pressure is reached. On deactivation, pressure holds in the cuff, thus in the "Power Off" mode, pressure is maintained.

Accordingly, it is an object of the present invention to provide a cuff inflation system that is provided with two external tubular connections, one of which is fastened to a blood pressure cuff and the other fastened to a pressure adjusting device.

It is a further object of this invention to provide a cuff inflation system that is adaptable for use with small pressure cuffs used for digit and penile inflation.

Another object of this invention is to provide a cuff inflation system wherein cuff damage resulting from over-inflation is obviated.

A still further object of this invention is to provide a cuff inflation system that does not require periodic calibration thereby indicating a true pressure level when in use.

A further object of this invention is to provide a cuff inflation system that enables an operator to deflate and inflate a cuff thereby facilitating vascular study when a series of cuffs are used.

Another object of this invention is to provide a cuff inflation system that has simplified controls thus providing operators with a more efficient device.

A still further object of this invention is to provide a cuff inflation system with a single activating and deactivating switch that activates the system, holds pressure at a predetermined level and thus shuts the system down thereby preventing over-inflation of the cuff.

DETAILED DESCRIPTION OF THE PREFERRED EMBODIMENT

Figure 1A:
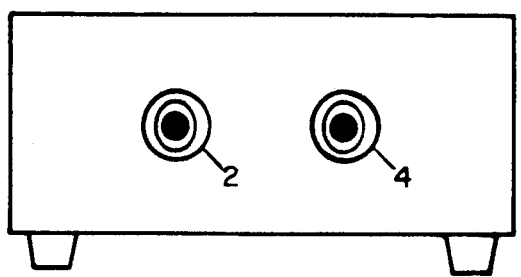
FIGS. 1a to 1d are views showing the exterior appearance of the activating and control assembly used in the cuff inflation system of this invention.
Figure 1B:
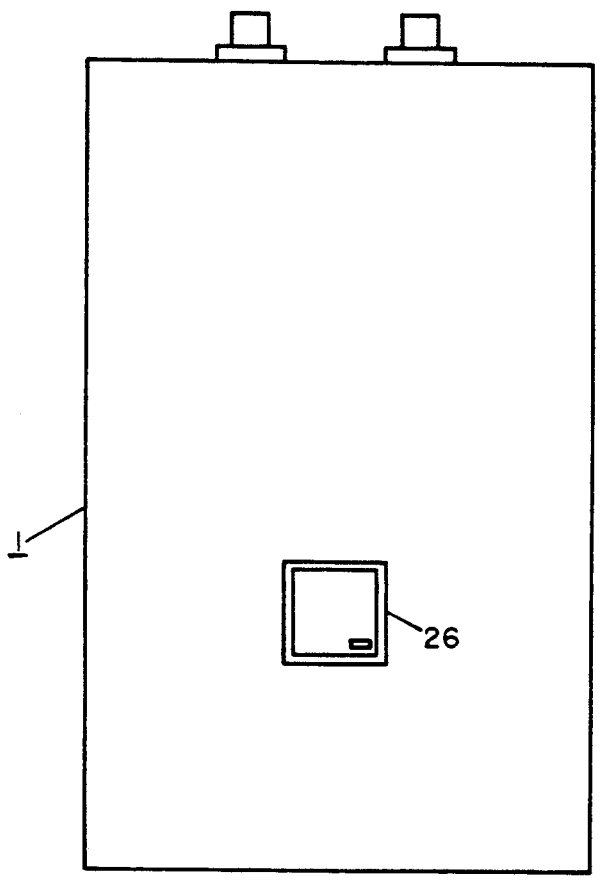
Figure 1C:
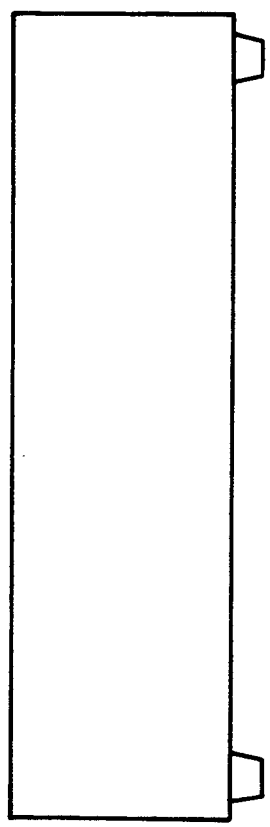
Figure 1D:
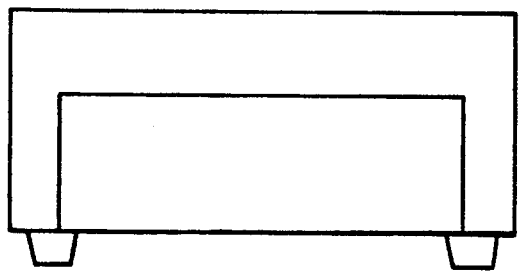

The cuff inflation system of this invention has a wide range of medical applications. It can be used for multiple sized blood pressure cuffs employed in measuring lower extremity blood pressures for diagnosing vascular disease. Typically, the cuffs used in vascular study range from large thigh cuffs to digit size. Large cuffs require an inflate pressure of up to 250 mm mercury and a large air volume. This invention accommodates a pressure buildup and volume of this magnitude. The pressure level is easily monitored by the operator utilizing the mercury manometer or sphygmomanometer connected to the system. Thus, the operator is afforded the convenience of manually inflating and deflating the blood pressure cuff as well as monitoring the cuff pressure. It is common practice not to use small cuffs with an inflator because cuff damage can result from overinflation. This invention, employing a sphygmomanometer attached to a second connection allows "hand inflation" of small cuffs. Thus, in multiple cuff testing as used in diagnosing vascular disease an operator can hand inflate small cuffs, directly inflate large cuffs and accurately control pressure levels without undertaking any disconnections. Using this invention leads to operator efficiency and increased testing performance while at the same time eliminating ruptured small cuffs that are common when powerful cuff inflators are used.

Utilizing the invention disclosed herein obviates the need to calibrate inflators. By employing a mercury manometer in the system, cuff pressure is readily available. When the invention is used with a sphygmomanometer, a mercury manometer can be placed in line via a three way stop cock at the cuff connection site. Therefore, testing can continue to be on line with the patient while readily determining pressure without the need to go off line for calibration.

Certain diagnostic testing such as vascular pulse-volume testing requires precisely holding the pressure level to 60 mm Hg. This invention allows an operator precise access to this pressure level The invention rapidly inflates the cuff to approximately 60 mm Hg and then the sphygmomanometer connection provides incremental adjustment to the precise level by deflation or inflation. Prior art devices are provided with only a bleed rate control to achieve deflation. Frequently the operator misses the desired level causing frustration as the cuff is inflated and then deflated, sometimes frequently, in order to attain the desired pressure level.

Doppler and pulse-volume testing procedures utilize multiple cuffs. Cuffs of varying widths are wrapped around the upper thigh, lower thigh, calf, above the ankle and toe. Cuffs are inflated and deflated in sequence. The small cuffs (e.g. toe cuff) are inflated manually to avoid rupture because of the small air volumes needed. The other cuffs are inflated by the invention and then deflated. Partial inflation and deflation by the sphygmomanometer is common. Therefore, this invention permits maximum flexibility for an operator because disconnections to accommodate small cuffs are not necessary.

Further medical advantages offered by the invention described herein include: a) the inflation of tourniquets while allowing the operator manual control of deflation and incremental inflation in emergency trauma cases; and b) Exerting and holding pressure when using intravenous fluid bags in hospitals.

Figure 2:
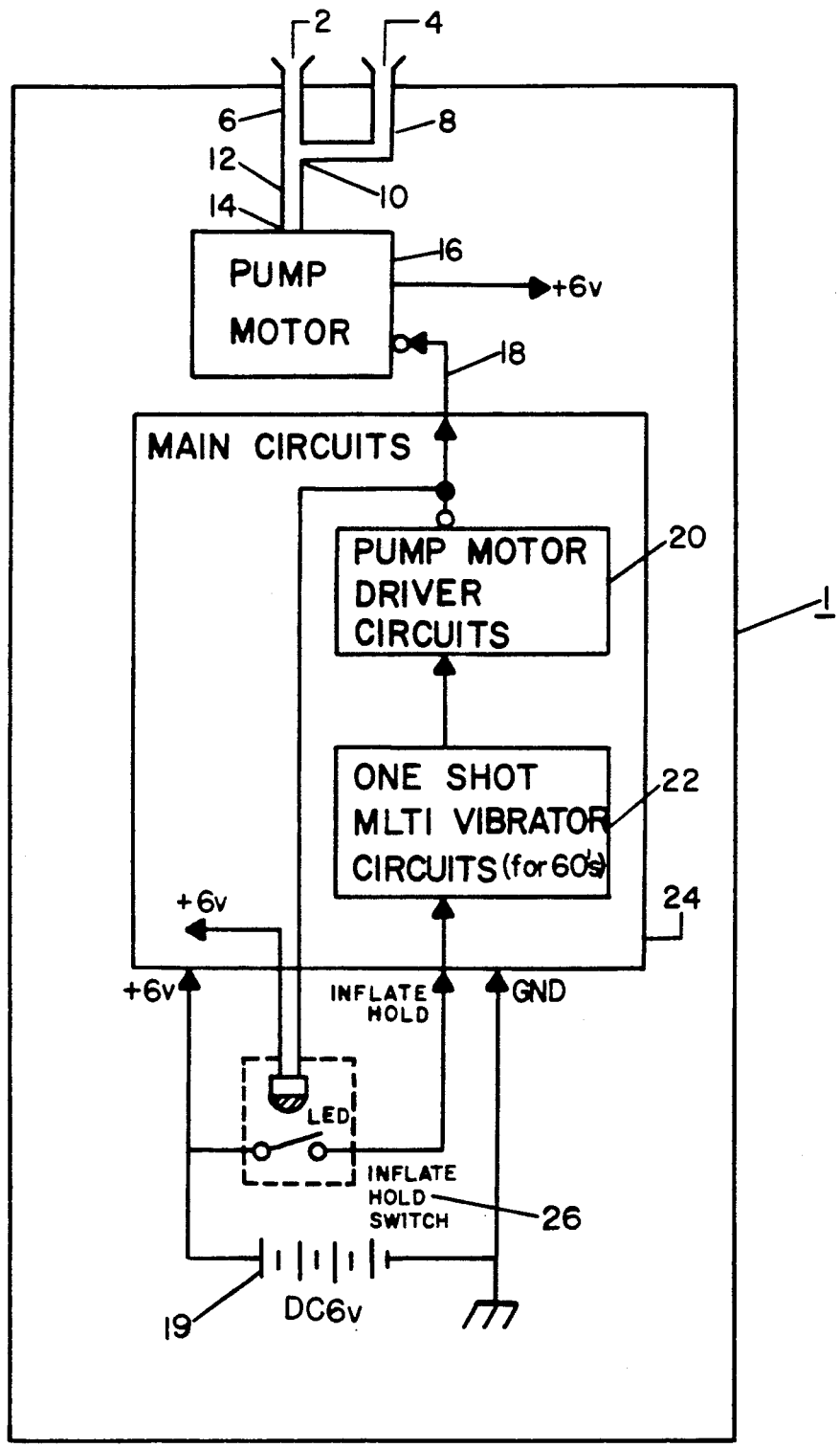
FIG. 2 is a block diagram that shows the activating and control assembly and electric circuits used in the cuff inflation system of this invention.
Figure 3:
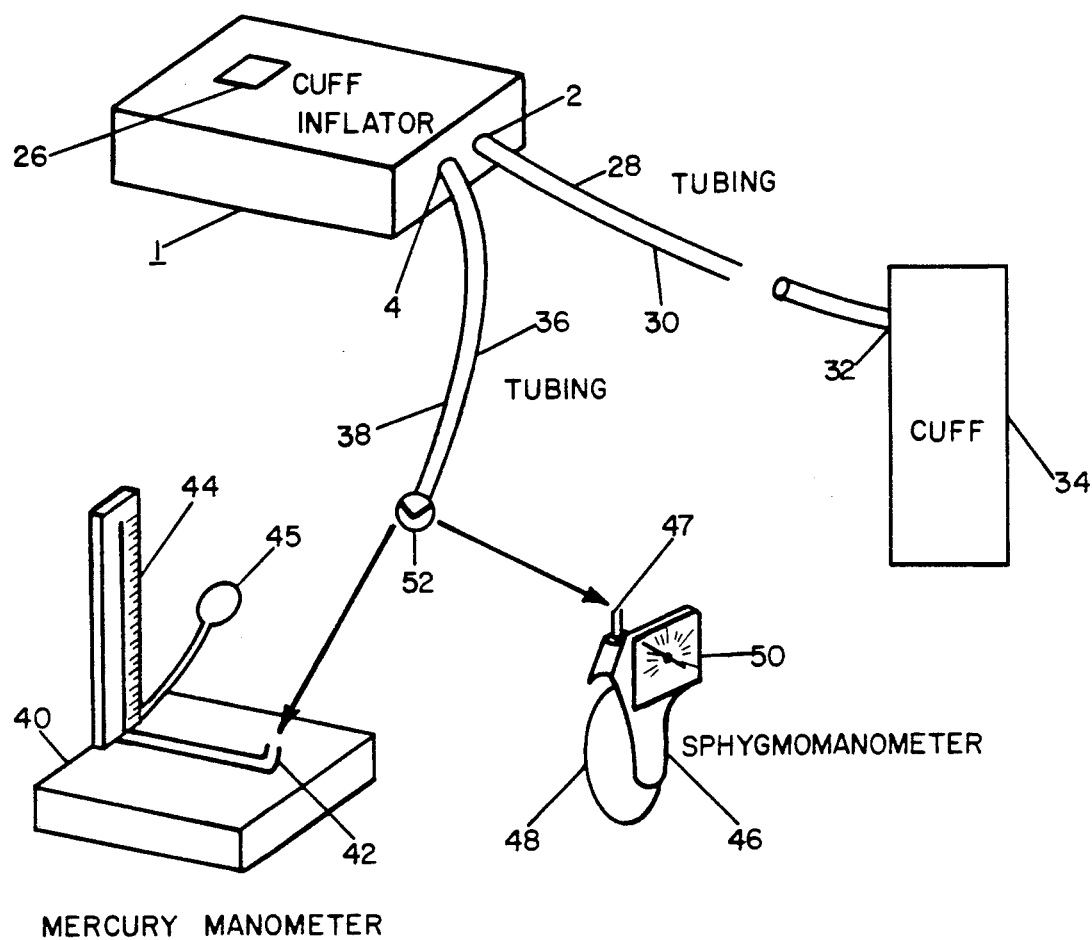
FIG. 3 is a schematic pictorial representation showing the cuff inflation system of this invention.

The cuff inflation system of this invention can be more fully understood by reference to FIGS. 1, 2 and 3. FIGS. 1a, b, c, and d show top, end and side views, respectively, of the exterior appearance of the activating and power control assembly 1 utilized in the system of this invention. As illustrated in FIG. 2, a block diagram shows the activating and power control assembly 1. A pair of female connector ports 2 and 4 are provided in the top end of assembly 1. Port 2 is provided with a first interior tube member 6 and port 4 is provided with a second interior tube member 8 that is further adapted to intersect and join tube 6 at juncture 10 so that a single tube is fastened at coupling 14 to a pump motor 16. Pump motor 16 is typically a six volt miniature pump that is energized by a low active signal emanating from power supply 18 consisting of an electric circuit and four double A alkaline batteries 19. Diagramically illustrated as numerical 20 is a pump motor driver circuit that serves to activate pump motor 16 and a one-shot multi-vibrator circuit 22 that functions to deactivate pump motor 16 if it is on for more than a predetermined time, typically more than one minute. Thus, circuit 22 acts as a sixty second clock that deactivates pump 16 after one minute of operation. An inflate hold circuit 24 maintains a constant pressure within the cuff inflation system and is electrically coupled to switch 26. When switch 26 is initially pressed, the inflate cycle is activated until a predetermined pressure level is reached, the switch is pressed a second time whereupon the inflation cycle is deactivated and the pressure level is maintained.

FIG. 3 illustrates the manner in which the activating and power control assembly is coupled with the other elements of this invention. A first tubular connector assembly 28 is connected to first female connector port 2 in any conventional manner as by fastening or use of male couplings and consists of plastic tubing 30 generally PVC (poly vinyl chloride) and conventionally connected at end 32 to a blood pressure cuff 34. A second tubular connector assembly 36 is conventionally connected to second female connector port 4 and consists of plastic tubing 38 and is thereafter connected to a device for monitoring pressure. FIG. 3 shows two such devices, namely a mercury manometer 40 and a sphygmomanometer 46. Thus, second tubular assembly 36 can be conventionally connected to mercury manometer 40 at base coupling 42. Pressure can be determined by reference to calibrated mercury column 44. The manometer is further provided with inflation bulb 45. Alternately, second tubular assembly 36 can be conventionally connected to sphygmomanometer 46 at coupling 47. Sphygmomanometer 46 is provided with inflation bulb 48 and gauge 50 for reading inflation pressure. Bulbs 45 and 48 are hand held bulbs that allow manual inflation as well as incremental inflation and deflation of the cuff 34 as well as dumping pressure within cuff 34. A three way stop cock 52 may be provided in the system of this invention so that the mercury manometer 40 and sphygmomanometer 46 can be operated interchangeably thereby providing a very flexible and versatile system.

The cuff inflation system illustrated in FIG. 3 would be operated in the following manner: cuff 34 would be positioned by an operator on a patient's extremity, i.e., an arm or leg. Switch 26 would be pressed causing activation of pump motor 16, thereby inflating cuff 34 by air pressure flowing through first tubular connector assembly 28. Pressure within cuff 34 is monitored by using a mercury manometer 40 or sphygmomanometer 46 that causes air pressure to be diverted from first interior tube member 6 into second interior tube member 8. Diversion of air pressure enables pressure to be maintained at a predetermined level in cuff 34. After this level is attained, the operator presses switch 26 thereby deactivating pump 16. The pressure is then held at this level.

Figure 4:
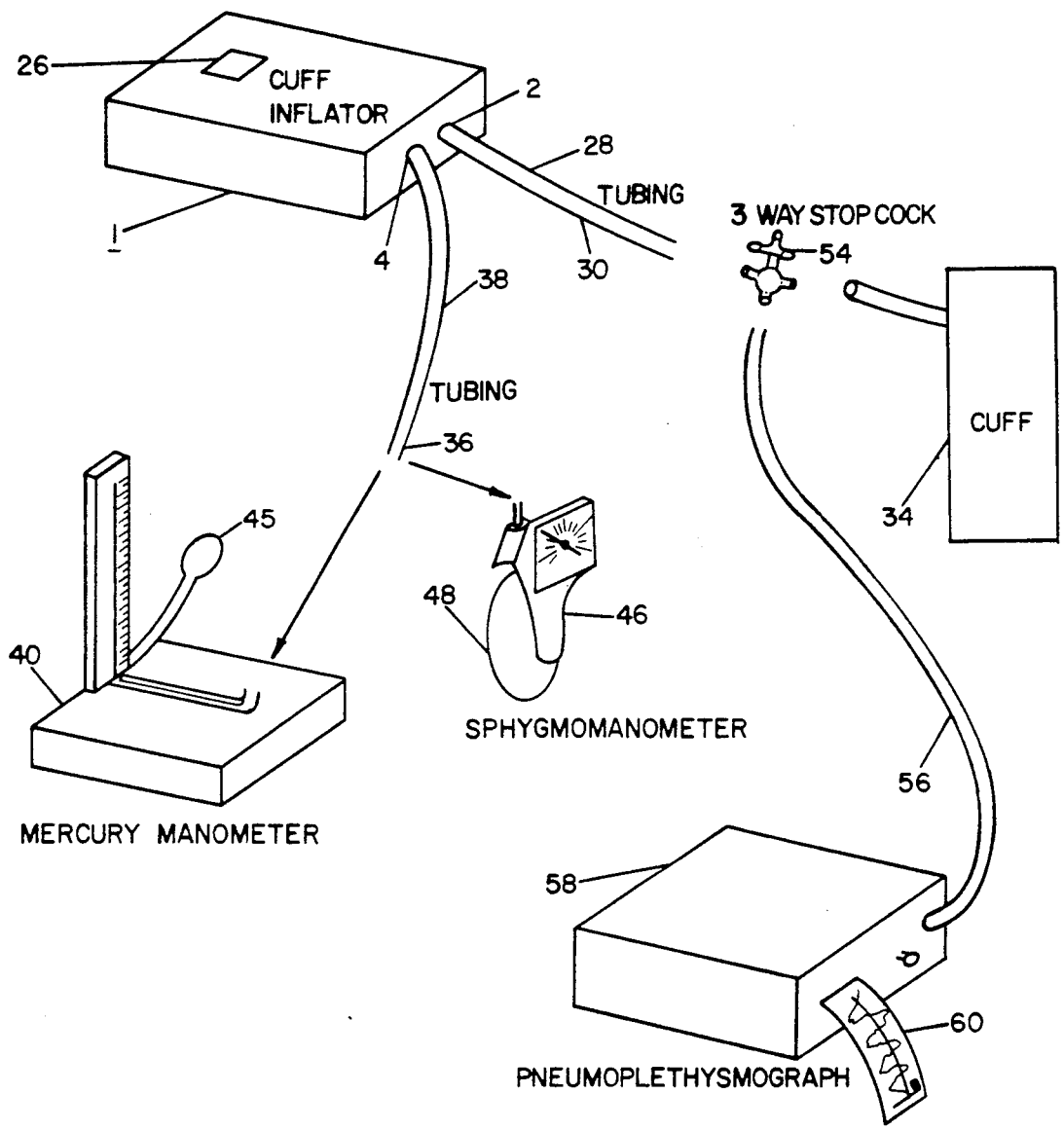
FIG. 4 is a schematic pictorial representation showing the cuff inflation system of this invention used in combination with a pneumoprinter and FIG. 4A shows a printout thereof.
Figure 4A:
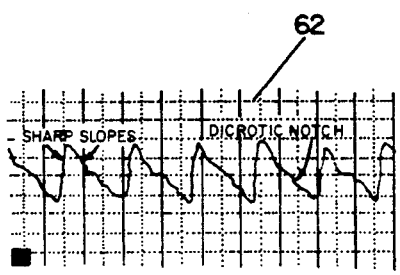

FIG. 4 illustrates the cuff inflation system of this invention used in the diagnosis of lower extremity peripheral artery disease. In this embodiment of the present invention a three way stop cock 54 is inserted into plastic tubing 30 thereby facilitating cuff 34 to be used in the manner as hereinbefore described or connect another section of plastic tubing 56 that is coupled to a pneumoplethysmograph or pneumoprinter 54. Cuff 34 is wrapped around a limb and is inflated in a manner described herein to a pressure of 60 mm Hg. Stop cock 54 is then positioned in such a manner that this 60 mm Hg level will cause pneumoprinter 58 to sense and print pneumo or pulse volume waveforms 60. This same test can be performed on a toe wherein a digit cuff is used and the inflation to 60 mm Hg will be achieved manually because of the small air volumes required. The invention will not have to be disconnected by the operator thus providing maximum flexibility of use. Numeral 62 in FIG. 4A illustrates an enlarged pulse wave form generated by this diagnostic procedure. Cuff inflation pressure is controlled and monitored by the operator using either mercury manometer 40 or sphygmomanometer 46.

Figure 5:
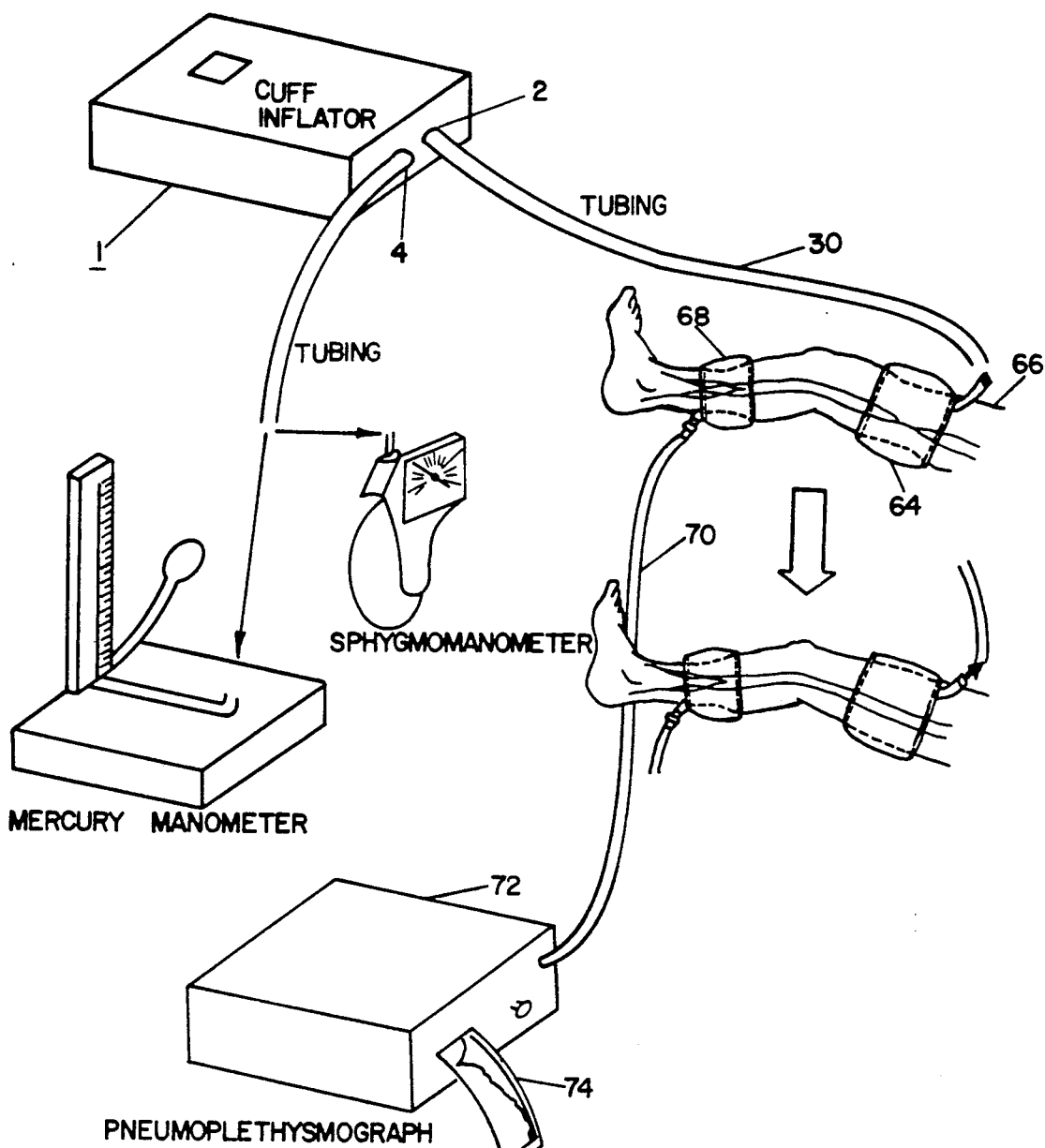
FIG. 5 is a schematic pictorial representation showing the cuff inflation system of this invention used with a plurality of blood pressure cuffs in combination with a pneumoprinter and FIG. 5A shows a printout thereof.
Figure 5A:
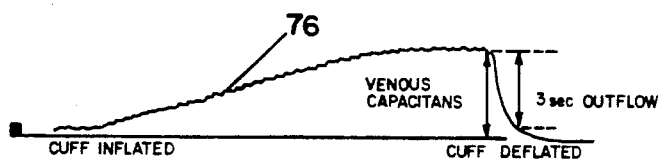

FIG. 5 illustrates another embodiment of the cuff inflation system of this invention. In this embodiment venous outflow is measured in order to diagnose deep venous thrombosis. Venous blood flow return from the calf to the Vena Cava is stopped by placement of an occlusive cuff 64 on the patient's thigh 66. A calf cuff 68 is attached to the patient and connected by plastic tubing 70 to a pneumoplethysmograph 72. After 90 seconds the patient's calf is caused to expand because of accumulated arterial flow. This results in compression of air in calf cuff 68 which is sensed and recorded by pneumoprinter 72. To conduct this type of diagnosis the cuff inflation system of this invention is used to inflate thigh cuff 64 to a pressure level of 60 mm Hg wherein switch 26 is pressed to deactivate pump 16. This inflation level is maintained by employing either mercury manometer 40 or sphygmomanometer 46 which is connected to second port 2. It has been found that by using sphygmomanometer 46 to adjust thigh cuff pressure level an operator has the ability to make incremental adjustments without fear of overshooting or undershooting the target pressure. To conduct a test utilizing the aforementioned arrangement, a test would commence by inflating thigh cuff 66 and calf cuff 68. Venous outflow is sensed and recorded by pneumoprinter 72. At the end of 90 seconds, thigh cuff 66 is deflated by an operator using sphygmanometer 46 or by disconnecting the thigh cuff from tubing 30. The rate of response to deflation is the diagnostic measurement of deep venous thrombosis. A schematic printout is illustrated at 74 and an enlarged schematic printout is shown by numeral 76 in FIG. 5A.

We claim:

1. A cuff inflation system for inflating a blood pressure cuff comprising:
   an activating and control assembly having a first connector port with an attached internal tube, a second connector port with an attached internal tube wherein said tube intersects and joins said first internal tube, an inflation means connected to said first internal tube, electric drive means for energizing said inflation means, means for maintaining inflation pressure, and an activating switch for activating said system;
   a first external tubular connector secured at one end to said first connector port and fastened at its opposite end to said blood pressure cuff;
   a pressure regulating and measuring means; and
   a second external tubular connector secured at one end to said second connector port and fastened at its opposite end to a said pressure regulating and measuring means.

2. The cuff inflation system of claim 1 wherein pressure regulating and measuring means is a mercury manometer and a hand pump.

3. The cuff inflation system of claim 1 wherein said pressure regulating and measuring means is a sphygmomanometer and a hand pump.

4. The cuff inflation system of claim 1 wherein said activating and control assembly further comprises a multi-vibrator circuit electrically connected to said electric drive means.

5. The cuff inflation system of claim 1 wherein said second external tubular connector further contains a three-way stop cock and a pair of tubular connectors secured to a mercury manometer and a sphygmomanometer.

6. A cuff inflation system for use with a blood pressure cuff in the diagnosis of lower extremity peripheral artery disease comprising: an activating and control assembly having a first connector port with an attached internal tube, a second connector port with an attached internal tube wherein said tube intersects and joins said first internal tube, an inflation means connected to said first internal tube, electric drive means for energizing said inflation means, means for maintaining inflation pressure, and an activating switch for activating said system;
   a first external tubular connector secured at one end to said first connector port, fastened at its opposite end to said blood pressure cuff and having a three-way stop cock located intermediate the ends of said connector;
   recording and print means connected to said stop cock for providing diagnostic data;
   a pressure regulating and measuring means; and
   a second eternal tubular connector secured at one end to said second connector port and fastened at its opposite end to a said pressure regulating and measuring means.

7. The cuff inflation system of claim 6 wherein said pressure regulating and measuring means is a mercury manometer and a hand pump.

8. The cuff inflation system of claim 6 wherein said pressure regulating and measuring means is a sphygmomanometer and a hand pump.

9. A cuff inflation system for use with a blood pressure cuff in the diagnosis of venous thrombosis comprising:

an activating and control assembly having a first connector port with an attached internal tube, a second connector port with an attached internal tube wherein said tube intersects and joins said first internal tube, an inflation means connected to said first internal tube, electric drive means for energizing said inflation means, means for maintaining inflation pressure, and an activating switch for activating said system;

a first external tubular connector secured at one end to said first connector port and fastened at its opposite end to said blood pressure cuff;

a second blood press adapted to be applied to a patient's calf;

a recording and printing means connected to said second cuff;

a pressure regulating and measuring means; and a second external tubular connector secured at one end to said connector and fastened at its opposite end to a said pressure regulating and measuring means.

10. The inflation system of claim 9 wherein said pressure regulating and measuring means is a mercury manometer and a hand pump.

11. The cuff inflation system of claim 9 wherein said pressure regulating and measuring means is a sphygmomanometer and a hand pump.

* * * * *